United States Patent
Hirata et al.

(10) Patent No.: US 7,144,589 B2
(45) Date of Patent: Dec. 5, 2006

(54) HIGH FUNCTIONAL WATER CONTAINING TITANIUM AND METHOD AND APPARATUS FOR PRODUCING THE SAME

(75) Inventors: Yoshihiro Hirata, Kyoto (JP); Yoshio Ueda, Kyoto (JP); Hiroaki Takase, Kyoto (JP); Kazuaki Suzuki, Kyoto (JP)

(73) Assignee: Phild Co., Ltd., Kyoto (JP)

( * ) Notice: Subject to any disclaimer, the term of this patent is extended or adjusted under 35 U.S.C. 154(b) by 637 days.

(21) Appl. No.: 10/275,681

(22) PCT Filed: Nov. 29, 2000

(86) PCT No.: PCT/JP00/08395
§ 371 (c)(1),
(2), (4) Date: Apr. 29, 2003

(87) PCT Pub. No.: WO01/85621
PCT Pub. Date: Nov. 15, 2001

(65) Prior Publication Data
US 2005/0072272 A1    Apr. 7, 2005

(30) Foreign Application Priority Data
May 10, 2000  (JP)  .............. 2000-136932

(51) Int. Cl.
C01B 5/00    (2006.01)
A61K 33/24   (2006.01)
B01J 8/00    (2006.01)
(52) U.S. Cl. ............ 424/617; 422/187; 423/580.1
(58) Field of Classification Search ........... 423/580.1; 422/187, 190, 198; 424/617
See application file for complete search history.

(56) References Cited

U.S. PATENT DOCUMENTS

| | | | | |
|---|---|---|---|---|
| 5,558,783 | A * | 9/1996 | McGuinness | ............... 210/761 |
| 6,869,626 | B1  | 3/2005 | Hirata et al. | |
| 6,989,127 | B1  | 1/2006 | Hirata et al. | |
| 2004/0091552 | A1 | 5/2004 | Hirata et al. | |
| 2004/0107798 | A1 | 6/2004 | Hirata et al. | |
| 2004/0118244 | A1 | 6/2004 | Hirata et al. | |

FOREIGN PATENT DOCUMENTS

| | | |
|---|---|---|
| JP | 122662 | 12/1937 |
| JP | 04-122433 | 4/1992 |
| JP | 06-142659 | 5/1994 |
| JP | 10-298615 | 11/1998 |

OTHER PUBLICATIONS

Dong Sheng-Zhang, et al., "A Study of Hygienic Standard for Titanium in the Source of Drinking Water," Chinese Journal of Preventive Medicine, vol. 27, No. 1, 1993, pp. 26-28, no month.
Zhang K et al., "The Species of Titanium in Natural Water," Journal of West China University of Medical Sciences, vol. 22, No. 4, 1991, pp. 406-408, no date.

* cited by examiner

Primary Examiner—Wayne A. Langel
(74) Attorney, Agent, or Firm—Knobbe, Martens, Olson & Bear LLP

(57) ABSTRACT

This invention provides a method and apparatus for manufacturing titanium-dissolved water with molten titanium dissolved therein, the molten titanium being titanium metal melted by the combustion gas resulting from the combustion of a mixed gas of oxygen and hydrogen in high-pressure water, as well as the resultant titanium-dissolved water and health articles, medical articles and cosmetics utilizing the physiologically activating effect of the high-function water containing titanium.

5 Claims, 2 Drawing Sheets

Flow chart for manufacturing titanium-containing water

[Figure 1]
Flow chart for manufacturing titanium-containing water
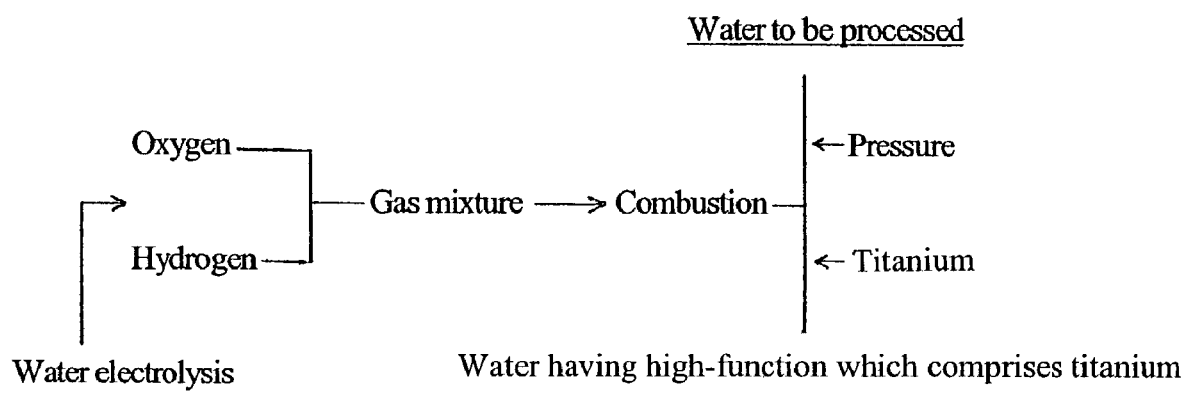

[Figure 2]
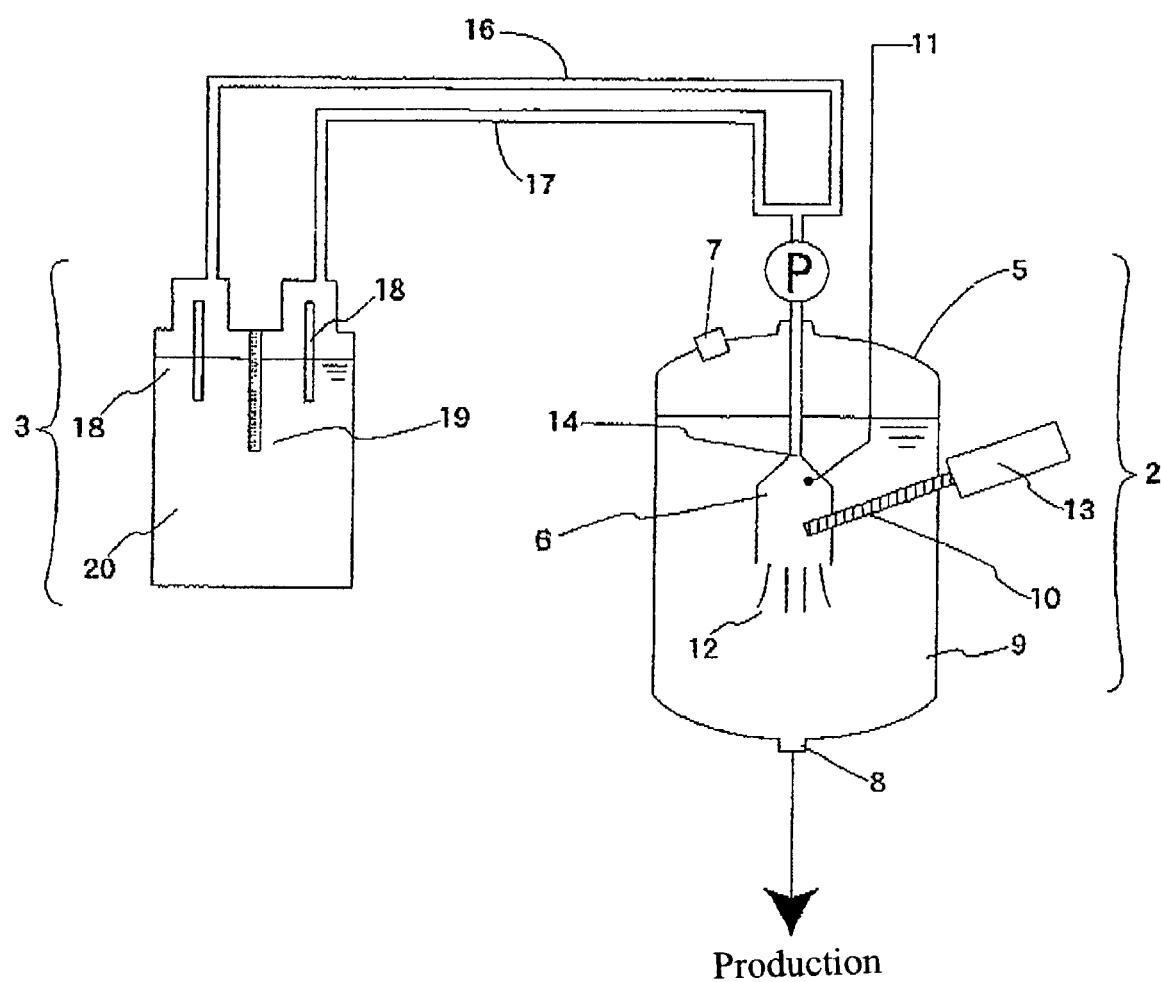

HIGH FUNCTIONAL WATER CONTAINING TITANIUM AND METHOD AND APPARATUS FOR PRODUCING THE SAME

FIELD OF THE INVENTION

This invention relates to high-function water with molten titanium dissolved therein and a method and apparatus for manufacturing the same.

The invention also relates to health articles, medical articles or cosmetics that employ the aforementioned high-function water.

BACKGROUND OF THE INVENTION

Compared to such metals as iron, copper or aluminum, titanium is a relatively newly discovered metallic material. The physical properties of titanium—namely its low weight and high strength, the latter of which is exhibited even at high temperatures—have found use in many fields. In the industrial sector, titanium is used in jet engine in the aeronautics and space industry, and in the tubing and tube sheets in the heat exchangers of nuclear and thermal power generators in the energy industry. Titanium is also used in eyeglass frames, golf club heads and other articles of everyday life. The uses for titanium are expanding continually.

The use of titanium metal in everyday articles, health and medical articles and cosmetics is relatively well known. Examples include barber's scissors with titanium film coatings (Japanese Patent Application Laid-open No. 62-268584), the utilization of far-infrared rays through molten titanium metal (Japanese Patent Application Laid-open Nos. 61-59147, 1-155803 and 3-112849), bedding (Japanese Patent Application Laid-open No. 8-322695), cooking utensils (Japanese Patent Application Laid-open No. 9-140593), eye masks (Japanese Patent Application Laid-open No. 10-71168), health maintenance devices (Japanese Patent Application Laid-open Nos. 11-285541 and 11-285543), health bands (Registered Japanese Utility Model No. 3045835) and health slippers (Registered Japanese Utility Model No. 3061466).

On the other hand, few techniques are known with regard to the use of titanium metal in the manufacture of functional water and the like. One rare example is a drinking-water production system (Japanese Patent Application Laid-open No. 50-40779) that utilizes electro-osmosis with titanium metal used in a negative electrode.

DISCLOSURE OF THE INVENTION

While the prospects are very promising for the expanded use of titanium in the fields of physiologically activating materials, food materials, medical articles or the like, the true value of this material has not been fully determined.

This invention aims especially at introducing the apparently infinite utility of titanium to the fields of physiologically activating materials and health/medical articles.

The purpose of this invention is to provide high-function water containing molten titanium in a dissolved state, where titanium metal is melted by the combustion gas of hydrogen and oxygen in high-pressure water.

Another purpose of this invention is to employ high-function water offering the high physiologically activating function, as obtained in this invention, in health articles, medical articles or cosmetics.

Yet another purpose of this invention is to provide an efficient method and apparatus for the manufacture of high-function water containing molten titanium that would contribute to health and medical care for purposes of physiological activation.

In this invention, the water containing a little molten titanium metal in a dissolved state will hereinafter be referred to as "titanium-dissolved water."

The first characteristic of this invention is high-function water in which molten titanium is dissolved in water.

The second characteristic of this invention is health articles, medical articles or cosmetics whose main ingredient is the aforementioned high-function water.

The third characteristic of this invention is a method of manufacturing high-function water with molten titanium dissolved therein, by burning a mixed gas of oxygen and hydrogen in high-pressure water and melting titanium metal in the resultant combustion gas.

The fourth characteristic of this invention is an apparatus for manufacturing high-function water with molten titanium dissolved therein, which is constituted by a pressure-resistant vessel comprising a high-pressure water-containment tank, an injection nozzle for a mixed gas of oxygen and hydrogen, a titanium metal rod, an ignition apparatus and a combustion chamber.

The fifth characteristic of this invention is an apparatus for manufacturing high-function water with molten titanium dissolved therein as described under the fourth characteristic, wherein a water-electrolysis apparatus is added for generating a mixed gas of oxygen and hydrogen.

Titanium particulates or titanium oxide in a simple water dispersion or mixture will precipitate and separate out in a short period of time. The most important characteristic of the titanium-dissolved water obtained in this invention is that titanium, melted by combustion heat, does not precipitate or otherwise separate out but stays in a dissolved state in the water over an extended period of time. The correlative reaction between the water molecules and molten titanium in the titanium-dissolved water of this invention has an unexpectedly pronounced effect of turning the water into high-function water.

The high-function, titanium-dissolved water of this invention may be utilized in health articles such as a cream for increased motor function, medical articles such as antibacterial agents, and cosmetics such as UV blocking creams.

The titanium-dissolved water of this invention has the appropriate usage at the present, as shown in the foregoing, but should also convincingly become a revolutionary physiologically activating material that would capably meet the demands of the recent trend toward more health-conscious living. While the mechanism of water with molten titanium dissolved therein for being an effective physiological activator is unknown, the inventors of this invention are now assiduously investigating the chemical cause.

BRIEF DESCRIPTION OF THE DRAWINGS

FIG. 1 is a flow chart for manufacturing the titanium-dissolved water of this invention.

FIG. 2 is a schematic drawing of an apparatus for manufacturing the titanium-dissolved water of this invention.

DESCRIPTIONS OF THE SYMBOLS

2: Pressure-resistant vessel for manufacturing titanium water
3: Electrolysis apparatus/raw-gas generating apparatus
5: High-pressure water-containment tank
6: Combustion chamber 7: Pressure-regulating valve
8: Titanium water outlet
9: High-pressure water
10: Titanium metal rod
11: Ignition apparatus
12: Molten titanium metal
13: Supply cylinder
14: Mixed-gas injection nozzle
16: Hydrogen supply line
17: Oxygen supply line
18: Electrode
18': Electrode
19: Partition plate
20: Water.

BEST MODE FOR CARRYING OUT THE INVENTION

The titanium-dissolved water obtained in this invention is a new article that has not previously been manufactured. This invention also discloses a new method and apparatus for the manufacture of water containing molten titanium in a dissolved state, where titanium is melted by the combustion heat of oxygen and hydrogen, not by the generally used means of melting metals by heat, arc discharge or laser irradiation.

To elaborate, the inventors examined the efficient and economical manufacture of titanium-dissolved water and the provision of titanium-dissolved water for purposes of physiological activation. The examination resulted in a method of containing molten titanium in a dissolved state by burning hydrogen and oxygen and then heating a pure titanium metal rod inserted into the combustion atmosphere. The method includes an innovation of burning hydrogen and oxygen in high-pressure water so as not to generate substances other than water and titanium metal.

The manufacturing method under this invention requires the control of the amounts of hydrogen and oxygen to be burned, the reaction pressure and the amount of titanium metal supplied. The water manufactured in the aforementioned manufacturing method also contains some amount of titanium-oxide particulate, in addition to the dissolved molten titanium metal, which would require a filtration system as necessary.

An explanation, with reference to figures, follows on a method of manufacturing the titanium-dissolved water with titanium metal dissolved in high-pressure water, as shown previously, as well as an apparatus for carrying out the same.

FIG. 1 is a flow chart for manufacturing the titanium-dissolved water of this invention. FIG. 2 shows an apparatus for manufacturing the titanium-dissolved water of this invention.

As shown in FIG. 2, an apparatus for manufacturing the titanium-dissolved water of this invention is constituted by a pressure-resistant vessel 2 for manufacturing water with molten titanium dissolved therein, an electrolysis apparatus/raw-gas generating apparatus 3 and a filtration system (not shown) for the titanium-dissolved water.

The basic design of the pressure-resistant vessel 2 of this invention is an apparatus for manufacturing titanium-dissolved water with titanium metal dissolved therein, which is comprised of a high-pressure water-containment tank 5, an injection nozzle 14 for a mixed gas of oxygen and hydrogen, a combustion chamber 6, and a titanium metal rod 10. The water-electrolysis apparatus 3 to supply hydrogen and oxygen as raw materials, and a filtration system for the produced titanium-dissolved water, are added as adjuncts.

The pressure-resistant vessel 2 of this invention is constituted by the high-pressure water-containment tank 5 made of metal, preferably steel. The mixed gas of hydrogen and oxygen, which is generated by the electrolysis apparatus 3 and supplied through a hydrogen supply line 16 and an oxygen supply line 17, is injected under high pressure into the combustion chamber 6 in the high-pressure water-containment tank 5. The titanium metal rod 10 is gradually fed by a supply cylinder 13 into the interior of the combustion chamber 6 in keeping with the burned amount. An ignition apparatus 11 ignites the mixed gas of hydrogen and oxygen, and molten titanium metal is discharged into high-pressure water 9. The high-pressure water 9 containing the molten titanium is then taken outside through an outlet 8 at the bottom of the high-pressure water-containment tank, and is in turn filtered through a filtration system (not shown) as necessary.

While the raw-gas generating apparatus 3 may be substituted by high-pressure cylinders storing hydrogen and oxygen, the electrolysis of water in this invention has the advantages of supplying totally pure oxygen and hydrogen and facilitating the efficient supply of these raw gases as fuels.

In an example of generating hydrogen and oxygen as raw materials for the manufacture of water through the electrolysis of water 20 in the raw-gas generating apparatus 3, 18 and 18' are the cathode plate and anode plate, respectively. As mentioned in the foregoing, hydrogen and oxygen may well be supplied directly from the respective storage cylinders thereof to the high-pressure water-containment tank 5.

Hydrogen and oxygen, generated by electrolysis and supplied through the hydrogen supply line 16 and the oxygen supply line 17, are injected via a pump into the combustion chamber 6 through the nozzle 14 for complete combustion, whereupon the complete combustion of extremely hot water-vapor gas takes place. The pure titanium metal rod 10 is inserted into the combustion gas for heating and combustion. The titanium metal rod is inserted by the cylinder 13 by a fixed amount as required by the amount of combustion. The mixing ratio of hydrogen and oxygen for combustion must be strictly maintained at 2:1. The internal pressure of the high-pressure water-containment tank must also be controlled through installation of a pressure-regulating valve 7.

As molten titanium metal 12, heated to a high temperature and burned in the combustion chamber 6, is discharged from the combustion chamber 6 into the high-pressure water 9, part of the titanium is assumed to form a crystalline structure.

The creation of molten titanium in such a state in water leaves highly hydrophobic molten titanium in a stably dissolved state in the water, which will not precipitate even if a flocculating agent is added.

With the manufacturing method of this invention, an example of recommended conditions for the manufacture of titanium-dissolved water on a one-ton scale would be a mixed gas pressure of approximately 3.5 atmospheres and mixed-gas injection rate of approximately four to six liters per second into the high-pressure water-containment tank, where the water is under a pressure of approximately 1.5 to 2.5 atmospheres. Excessive gas pressure may risk damaging the structure of the apparatus. On the other hand, insufficient pressure will lower the molten titanium production as the gas is allowed to escape out of the combustion chamber and cause the heated, molten titanium metal to disperse, wrapped in bubbles, to the surface of the water.

To operate the apparatus, inject hydrogen and oxygen under high pressure via a pump into the high-pressure water-containment tank 5 through the nozzle 14. Ignite the gas by means of the ignition apparatus 11 to set up the combustion of extremely hot water-vapor gas. Insert the pure titanium metal rod 10 into the combustion gas and burn it.

It is essential to burn hydrogen and oxygen in water so as not to generate substances other than water and molten titanium metal in the apparatus. Hydrogen and oxygen must be burned in water under high pressure to prevent the introduction of impurities. Furthermore, the titanium metal rod must be inserted in an area where the mixed gas would be burnt completely and converted into extremely hot water-vapor gas.

Another characteristic of this invention is to appropriately refine the titanium-dissolved water with molten titanium dissolved therein, as manufactured in the foregoing, and use it as a raw material for health articles, cosmetics, foodstuffs, drugs, quasi-drugs and the like. The water produced contains some amount of titanium-oxide particulate and therefore requires filtration and refinement as necessary.

The preferred method of filtration is the use of the filtration system explained below, instead of ion exchange or reverse-osmotic membrane, to prevent the unnecessary elimination of the produced molten titanium and allow the production of water suitable for applications. That is, the use of a hollow-fiber membrane as a filter is preferable, and it is desirable with respect to the characteristics of the titanium-dissolved water and to the filter life if the high-pressure water discharged from the high-pressure water-containment tank is passed through sequential filters. The foregoing method enables the manufacture of drinking water that meets the food sanitation, cosmetics and drug standards.

When the inventors studied the content of the titanium-dissolved water obtained in this invention, it was confirmed that an extreme trace amount of molten titanium is contained in the high-pressure water.

The result of an analysis of the titanium-dissolved water obtained in this invention is shown below.

ASSAY REPORT (No. 200031801-006, Apr. 6, 2000)
   Client Name: Phild Co., Ltd.
   Specimen: TITANIUM-CONTAINING PURIFIED WATER FILTER 0.5
   Additional Remarks: ****
   By Japan Food Research Laboratories (Tokyo H.Q.: 52-1, Motoyoyogi-machi, Shibuya-ku, Tokyo 151-0062; Osaka Branch: 3-1, Toyotsu-cho, Suita-shi, Osaka 564-0081; Nagoya Branch: 5-13, Ohsu 4-chome, Naka-ku, Nagoya 450-0011; Kyushu Branch: 1-12, Shimogo-fuku-cho, Hakata-ku, Fukuoka 812-0034; Tama Research Laboratory: 11-10, Nagayama 8-chome, Tama-shi, Tokyo 206-0025)
   The followings are analysis results for the above-identified specimen that was submitted to the laboratory on Mar. 31, 2000.

| Assay Item | Results | Detection Limit | Notes | Analysis Method |
|---|---|---|---|---|
| Titanium | 0.72 mg/L | | | ICP Luminescence Analysis Method |

(This experiment was conducted after excluding precipitations.)

The following is a specific explanation of an embodiment of this invention using an example. However, the invention is not limited to the example provided.

[Embodiment]

FIG. 2 shows a representative embodiment of an apparatus under this invention for manufacturing titanium-dissolved water with titanium metal dissolved therein, where titanium metal is melted by water molecules under water. The apparatus comprises a high-pressure water-containment tank 5, an injection nozzle for a mixed gas of oxygen and hydrogen 14 and a titanium metal rod 10.

The high-pressure water-containment tank 5 is a pressure-resistant tank, made of metal, that can withstand extremely high pressure, and wherein a mixed gas of hydrogen and oxygen, supplied through a hydrogen supply line 16 and an oxygen supply line 17, is injected through the injection nozzle 14 into a combustion chamber 6, and the titanium metal rod 10 is fed into the combustion chamber by a cylinder 13. The internal pressure of the high-pressure water-containment tank 5 must be controlled by a pressure-regulating valve 7. An ignition apparatus 11 ignites a mixed gas, and molten titanium 12 is discharged into high-pressure water. The titanium-dissolved water with titanium metal dissolved therein is taken outside through an outlet 8.

To operate the apparatus, as mentioned in the foregoing, supply hydrogen and oxygen into the high-pressure water-containment tank 5 under high pressure and inject the mixed gas through the nozzle 14. Ignite the mixed gas by means of the ignition apparatus 11 to burn the gas completely in order to set up the complete combustion of extremely hot water-vapor gas. Insert the pure titanium metal rod 10 into the combustion gas and burn it. It is assumed that when the molten titanium 12, heated to a high temperature in the nozzle, is discharged into the high-pressure water, part of the titanium metal forms a crystalline structure, and that the titanium atoms realign themselves to form a near sphere, thereby achieving a stable state in terms of energy.

The titanium-dissolved water thus produced has molten titanium dissolved in the water without the aid of an activator. The produced titanium-dissolved water is discharged from the outlet and sent to a filtering system as necessary. The filtering system sequentially comprises 50-, 25-, 3-, 0.5- and 0.1-micron filters to ultimately yield titanium-dissolved water containing an extreme trace amount of molten titanium metal.

Embodying Conditions (Example)
   Manufacturing tank internal pressure: 2 atmospheres
   Mixed gas: 5 liters/sec. (3.5 atmospheres)
   Titanium metal supply amount: 0.5 kg/2 hours
   Produced titanium-dissolved water: 1,000 kg.

The foregoing conditions yielded titanium-dissolved water with titanium metal dissolved therein.

The produced titanium-dissolved water is filtered (sequentially through a 50-, 25-, 3-, 0.5 and 0.1-micron hollow-fiber membranes) as necessary.

Test of the Use of High-Function Water

The titanium-dissolved water, which is water with titanium dissolved therein, was topically applied or sprayed on a group of ten male and female monitors to test for the effect and efficacy of the water on the promotion of health and its physiologically activating capabilities.

Testing Conditions and Monitoring Results
1. Total number of monitors: 10 men and women (in non-regular trial usage)
2. Examples of efficacy
   The body felt light: 5 persons
   Tiredness was reduced: 8 persons
   Recovery from tiredness was fast: 7 persons
   Cold symptoms improved significantly: 1 person
   Motor ability improved (bending forward, broad jump, etc.): 6 persons
   The skin became smooth: 7 persons
   Stiff shoulders improved significantly: 7 persons
   Recovered from tired eyes: 3 persons
   Wounds healed quickly: 1 person.

Evaluation of Test Results

The frequent occurrence of recoveries from tiredness, improved motor function, recoveries from stiff shoulders, smoother skin and the like among the monitors that had topically applied or sprayed the titanium-dissolved water on their bodies revealed that the titanium-dissolved water of this invention exhibits a pronounced effect as a raw material for health articles, medical articles or cosmetics.

INDUSTRIAL APPLICABILITY

This invention provides a new titanium-dissolved water and a method and apparatus for manufacturing the same, which enables the efficient manufacture of water containing molten titanium in a dissolved state and having a physiologically activating function. The monitoring tests revealed that the titanium-dissolved water obtained is capable of being utilized in health articles, medical articles and cosmetics. Additionally, the results of a drinking test especially promise a potentially pronounced effect as health water.

What is claimed is:

1. Water in which molten titanium is dissolved in water.

2. A topical cream or liquid comprising the water as described in claim 1.

3. A method of manufacturing water with molten titanium dissolved therein, by burning a mixed gas of oxygen and hydrogen in high-pressure water and melting titanium metal in the combustion gas resulting from the step of burning the mixed gas of oxygen and hydrogen.

4. An apparatus for manufacturing water with molten titanium dissolved therein, comprising a high-pressure water-containment tank, an injection nozzle for a mixed gas of oxygen and hydrogen, a titanium metal rod, an ignition apparatus and a combustion chamber.

5. The apparatus for manufacturing water as described in claim 4, further comprising a water-electrolysis apparatus for generating the mixed gas of oxygen and hydrogen, disposed upstream of the injection nozzle.

* * * * *